United States Patent [19]

Janssen et al.

[11] Patent Number: 5,480,912
[45] Date of Patent: * Jan. 2, 1996

[54] METHOD OF TREATING HIV-1 WITH α-SUBSTITUTED BENZENEMETHANAMINE DERIVATIVES

[75] Inventors: Marcel A. C. Janssen, Vosselaar; Georges H. P. Van Daele, Turnhout; Jean-Paul R. M. A. Bosmans, Edegem; Frans M. A. Van den Keybus, Essen; Karin J. M. M. Nuyens, Brecht; Paul A. J. Janssen, Vosselaar, all of Belgium

[73] Assignee: Janssen Pharmaceutica, N.V., Belgium

[*] Notice: The portion of the term of this patent subsequent to Apr. 18, 2012, has been disclaimed.

[21] Appl. No.: 400,218

[22] Filed: Mar. 7, 1995

Related U.S. Application Data

[62] Division of Ser. No. 240,735, May 12, 1994, Pat. No. 5,407,961.

[30] Foreign Application Priority Data

Dec. 30, 1991 [EP] European Pat. Off. ............ 91203430

[51] Int. Cl.$^6$ ................ A61K 31/135; A61K 31/34; A61K 31/35; A61K 31/365
[52] U.S. Cl. ................ 514/649; 514/259; 514/311; 514/312; 514/418; 514/456; 514/469; 514/470; 514/603; 514/620; 514/639; 514/640; 514/653
[58] Field of Search ................ 514/259, 311, 514/312, 418, 456, 469, 470, 603, 620, 639, 640, 649, 653

[56] References Cited

U.S. PATENT DOCUMENTS 4,246,429  1/1981  Van Daele ................ 562/456

FOREIGN PATENT DOCUMENTS 0006713  1/1980  European Pat. Off. .
WO92/00952  1/1992  WIPO .

Primary Examiner—Richard L. Raymond
Attorney, Agent, or Firm—Charles J. Metz

[57] ABSTRACT

The present invention is concerned with antiretroviral (e.g. anti HIV-1) compounds having the formula

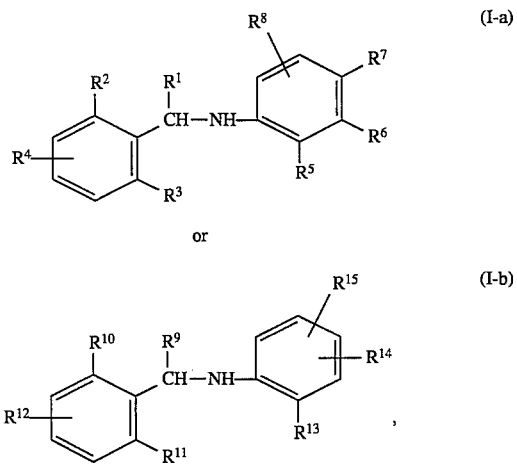

Pharmaceutical compositions containing said compounds of formula (I-a) or (I-b), and processes of preparing said compounds and compositions.

5 Claims, No Drawings

METHOD OF TREATING HIV-1 WITH α-SUBSTITUTED BENZENEMETHANAMINE DERIVATIVES

CROSS-REFERENCE TO RELATED APPLICATIONS

This application is a division of application Ser. No. 08/240,735, filed May 12, 1994, now U.S. Pat. No. 5,407,961, which was based upon PCT Application No. PCT/EP 92/02995, filed Dec. 22, 1992, which claims priority from EPO application Ser. No. 91.203.430.3, filed Dec. 30, 1991.

BACKGROUND OF THE INVENTION

In U.S. Pat. No. 4,246,429 there are described a number of benzeneacetamides and thioamides being useful as intermediates in the preparation of phytopharmaceutical compounds. Unexpectedly, it has now been found that some analogous intermediates effectively inhibit the replication of HIV and consequently may be useful for the treatment of individuals infected by HIV, in particular HIV-1.

DESCRIPTION OF THE INVENTION

The present invention is concerned with compounds having the formula

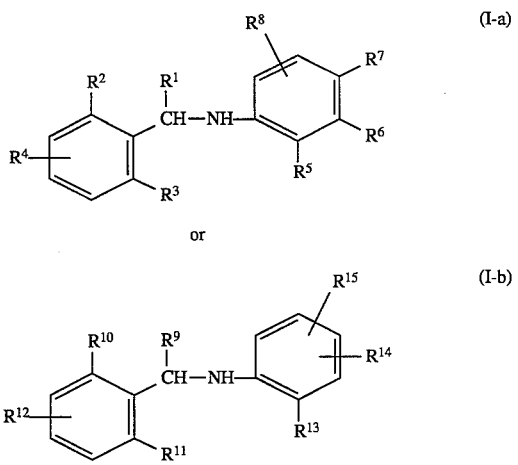

the pharmaceutically acceptable acid addition salts thereof and the stereochemically isomers forms thereof, wherein $R^1$ is trifluoromethyl; methylcarbonyl or $C_{3-6}$cycloalkyl; or a radical $-C(=X)-NR^{16}R^{17}$, wherein X is O or S, and $R^{16}$ and $R^{17}$ each independently are hydrogen or $C_{1-4}$alkyl; or a radical $-Alk-R^{18}$, wherein Alk is $C_{1-4}$alkanediyl, and $R^{18}$ is hydrogen or hydroxy;

$R^2$ and $R^3$ each independently are halo or methyl;

$R^4$ is hydrogen, hydroxy, halo, nitro, or trifluoromethyl;

$R^8$ represents hydrogen, $C_{1-6}$alkyloxy, $C_{1-6}$alkyl, halo, nitro, aminocarbonyl, or a radical $C_{1-6}$alkyl—(C=Z)—, wherein Z represents O, N—OH, N—OCH$_3$, N—NH$_2$ or N—N(CH$_3$)$_2$;

$R^7$ represents hydrogen, in which case $R^5$ and $R^6$ taken together form a bivalent radical of formula $(CH_2)_m$ wherein m is 3 or 4, —(C=O)—O—CH$_2$—, —(C=O)—O—(CH$_2$)$_2$—, —(C=O)—(CH$_2$)$_2$—, —(C=O)—(CH$_2$)$_3$—, —(C=O)—CH$_2$—O—, —(C=O)—CH$_2$—NH—, —(C=O)—(CH$_2$)$_2$—O—, —O—(CH$_2$)$_2$—, —O—(CH$_2$)$_3$—, —N=CH—CH=CH—, —(N→O)=CH—CH=CH— or —(C=O)—NH—CH=N—, wherein one or two hydrogen atoms can optionally be replaced with $C_{1-4}$alkyl; or $R^6$ and $R^7$ taken together form a bivalent radical of formula —(CH$_2$)$_m$— wherein m is 3 or 4 and wherein one or two hydrogen atoms can optionally be replaced with $C_{1-4}$alkyl, in which case $R^5$ represents hydrogen, $C_{1-6}$alkyloxy, $C_{1-6}$alkyl, halo, nitro, aminocarbonyl, or a radical $C_{1-6}$alkyl—(C=Z), wherein Z is as defined hereinabove;

$R^9$ is trifluoromethyl, methylcarbonyl or $C_{3-6}$cycloalkyl; or a radical —Alk—$R^{19}$, wherein Alk is $C_{1-4}$alkanediyl; and $R^{19}$ is hydrogen or hydroxy;

$R^{10}$ and $R^{11}$ each independently are halo or methyl;

$R^{12}$ is hydrogen, hydroxy, halo, nitro or trifluoromethyl;

$R^{13}$ represents $C_{1-6}$alkyloxy, nitro, trifluoromethoxy, 2,2,2-trifluoroethoxy, (trifluoromethyl)carbonyl, aminocarbonyl, (cyclopropyl)carbonyl or a radical $C_{1-6}$alkyl—C(=Z)— wherein Z is defined as hereinabove; and $R^{14}$ and $R^{15}$ each independently are hydrogen, halo, $C_{1-4}$alkyl, nitro, $C_{1-4}$alkyloxy or trifluoromethyl.

The compounds of formula (I) wherein at least one of $R^{16}$ and $R^{17}$ is hydrogen may also exist in their tautomeric form. Said form although not explicitly indicated hereinabove is intended to be included within the scope of the present invention.

In the foregoing definitions halo defines fluoro, chloro, bromo and iodo; $C_{1-4}$alkyl defines straight and branch chained saturated hydrocarbon radicals having from 1 to 4 carbon atoms, such as, for example, methyl, ethyl, propyl, 1-methylethyl, butyl, 1-methylpropyl, 2-methylpropyl, and 1,1-dimethylethyl; $C_{1-6}$alkyl defines $C_{1-4}$alkyl and the higher homologs thereof having 5 or 6 carbon atoms, such as, for example, pentyl, hexyl and the like; $C_{1-4}$alkanediyl defines bivalent straight or branch chained hydrocarbon radicals containing from 1 to 4 atoms, such as, fox example, 1,2-ethanediyl, 1,3-propanediyl, 1,4-butanediyl and the branched isomers thereof; $C_{3-6}$cycloalkyl defines cyclopropyl, cyclobutyl, cyclopentyl or cyclohexyl.

The pharmaceutically acceptable acid addition salts as mentioned hereinabove comprise the therapeutically active non-toxic acid addition salt forms which the compounds of formula (I-a) or (I-b) are able to form. Said salts can conveniently be obtained by treating the base form of the compounds of formula (I-a) or (I-b) with appropriate acids such as inorganic acids, for example, hydrohalic acid, e.g. hydrochloric, hydrobromic and the like acids, sulfuric acid, nitric acid, phosphoric acid and the like; or organic acids, such as, for example, acetic, hydroxyacetic, propanoic, 2-hydroxypropanoic, 2-oxo-propanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propane-tricarboxylic, methanesulfonic, ethanesulfonic, benzene-sulfonic, 4-methylbenzene-sulfonic, cyclohexanesulfamic, 2-hydroxybenzoic, 4-amino-2-hydroxybenzoic and the like acids. Conversely the salt form can be convened by treatment with alkali into the free base form. The term acid addition salt also comprises the hydrates and solvent addition/brms which the compounds of formula (I-a) or (I-b) are able to form. Examples of such forms are e.g. hydrates, alcoholales and the like.

The term "stereochemically isomeric forms" as used hereinbefore defines the different isomeric forms which the compounds of formula (I) may possess. Unless otherwise mentioned or indicated, the chemical designation of compounds denotes the mixture of all possible stereochemically isomeric forms, said mixtures containing all diastereomers, and/or enantiomers of the basic molecular structure. All stereochemically isomeric forms of the compounds of formula (I) both in pure form or in admixture with each other are intended to be embraced within the scope of the present invention.

Interesting compounds are those compounds of formula (I-a), wherein $R^1$ is a radical —C(=X)NR$^{16}$R$^{17}$, wherein X is O or S, $R^{16}$ and $R^{17}$ each independently are hydrogen or $C_{1-4}$alkyl; $R^2$ and $R^3$ are halo; and $R^4$ is hydrogen or halo.

More interesting compounds are those interesting compounds of formula (I-a), wherein $R^1$ represents a radical —CONH$_2$; $R^8$ represents halo, $C_{1-4}$alkyl or $C_{1-4}$alkylcarbonyl; and $R^7$ represents hydrogen when $R^5$ and $R^6$ taken together form a bivalent radical of formula —(C=O)—O—CH$_2$—, —(C—O)—O—(CH$_2$)$_2$—, —(C=)—(CH )$_2$—, —(C=O)≧(CH$_2$)$_3$—, —(C=O)—CH$_2$—O—, —(C=O)—(CH$_2$)$_2$—O—, —O—(CH$_2$)$_2$—, —O—(CH$_2$)$_3$—, or —(N→O)=CH—CH=CH—; or $R^6$ and $R^7$ taken together form a bivalent radical of formula —(CH$_2$)$_m$— wherein m represents 3 or 4 and $R^5$ represents hydrogen or $C_{1-4}$alkylcarbonyl.

Particularly interesting compounds are those more interesting compounds of formula (I-a) wherein $R^8$ represents fluoro, chloro, bromo, methyl or methylcarbonyl; and $R^7$ represents hydrogen when $R^5$ and $R^6$ taken together form a bivalent radical of formula —(C=O)—O—CH$_2$, —(C=O)—(C$_2$)$_2$—, —(C=O)—CH$_2$—O—, —O—(CH$_2$)$_2$—, or —(N→O)=CH—CH=CH—; or $R^6$ and $R^7$ taken together form a bivalent radical of formula —(CH$_2$)$_3$— and $R^5$ represents hydrogen.

Preferred compounds of formula (I-a) are:
α-[(6-acetyl-2,3-dihydro-1H-inden-5-yl)amino]-2,6-dichlorobenzeneacetamide;
2,6-dichloro-α-[(5-chloro-2,3-dihydro-7-benzofuranyl)amino]benzeneacetamide;
2,6-dichloro-α-[(2,3-dihydro-6-methyl-3-oxo-1H-inden-4-yl)amino]benzeneacetamide;
2,6-dichloro-α-(8-quinolinylamino )benzeneacetamide-1-oxide;
2,6-dichloro-α-[(2,3-dihydro-3-oxo-4-benzofuranyl)amino] benzeneacetamide, the pharmaceutically acceptable acid addition salts and the stereochemically isomeric forms thereof.

Other interesting compounds are those compounds of formula (I-b), wherein $R^9$ is cyclopropyl or a radical —Alk—R$^{19}$, $R^{10}$ and $R^{11}$ are halo; and $R^{12}$ is hydrogen or halo.

More interesting compounds are those interesting compounds of formula (I-b), wherein $R^9$ is cyclopropyl, methyl, ethyl or hydroxymethyl; $R^{13}$ represents $C_{1-4}$alkyloxy, nitro or $C_{1-4}$alkylcarbonyl; and $R^{14}$ and $R^{15}$ each independently represent hydrogen or $C_{1-4}$alkyl.

Particularly interesting compounds are those more interesting compounds of formula (I-b), wherein $R^{13}$ represents nitro or methylcarbonyl; and $R^{14}$ and $R^{15}$ represent hydrogen.

Preferred compounds of formula (I-b) are:
2,6-dichloro-a-methyl-N-(2-nitrophenyl)benzenemethanamine.
1-[2-[[ 1-(2,6-dichlorophenyl)ethyllamino]phenyl]ethanone;
2,6-dichloro-β-[(2-nitrophenyl)amino]benzeneethanol;
1-[2-[[1-(2,6-dichlorophenyl)propyl]amino]phenyl]ethanone;
1-[2-[[cyclopropyl(2,6-dichlorophenyl)methyl]amino]phenyl]ethanone;
the pharmaceutically acceptable acid addition salts and the stereochemically isomeric forms thereof.

The compounds of formula (I-a) can generally be prepared by reacting an intermediate of formula (II-a) with an appropriate bicyclic derivative of formula (III-a)

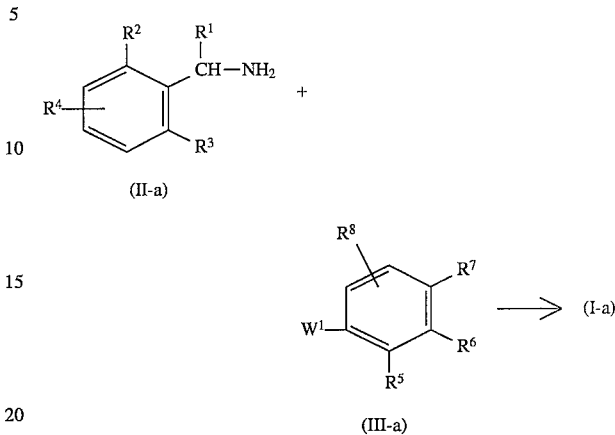

In formula (III-a) $W^1$ represents a reactive leaving group, such as, for example, halo, $C_{1-6}$alkyloxy, aryloxy, ($C_{1-6}$alkyl or aryl)sulfonyloxy, ($C_{1-6}$alkyl or aryl)sulfonyl, $C_{1-6}$alkylthio or nitro, preferably fluoro, bromo, chloro, nitro, 4-methylbenzenesulfonyloxy, methoxy or methylthio.

The compounds of formula (1-b) can generally be prepared in an analogous way by reacting an intermediate of formula (II-b) with an appropriate benzenederivative (III-b).

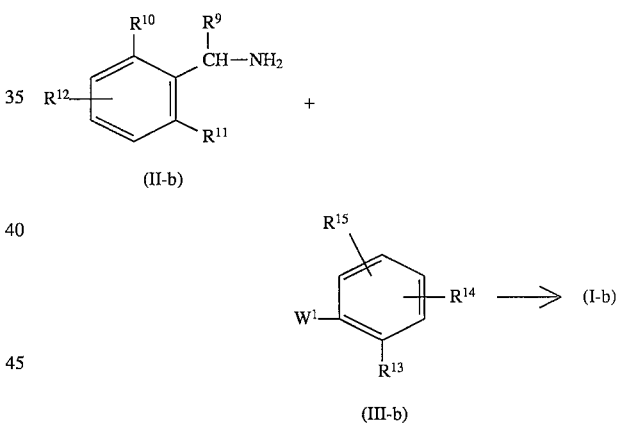

In formula (Ill-b) $W^1$ represents a leaving group as defined above. The above reactions can be performed by stirring the reactants, preferably at an elevated temperature and in particular at the reflux temperature of the reaction mixture, whereby an excess of one of the reactants can be used as solvent; or optionally in admixture with an appropriate solvent such as, for example, a dipolar aprotic solvent, e.g. N,N-dimethylformamide, N,N-dimethylacetamide, dimethylsulfoxide, 1-methyl-2-pyrrolidinone, acetonitrile; an ether, e.g. tetrahydrofuran, 1,1'-oxybisethane, 1,4-dioxane and the like; and mixtures of such solvents.

An appropriate base such as, for example, an alkali metal or an earth alkaline metal carbonate, hydrogen carbonate, hydroxide, oxide, carboxylate, alkoxide, hydride or amide, e.g. sodium carbonate, sodium hydrogen carbonate, potassium carbonate, sodium hydroxide, calcium oxide, sodium acetate, sodium methoxide and the like, or an organic base such as, for example, an amine, e.g. N,N-diethylethanamine, N-( 1-methylethyl)-2-propanamine, 4-ethylmorpholine, 1,4- diazabicyclo[2.2.2]octane, pyridine and the like, may optionally be used to pick up the acid which is formed during the course of the reaction. Additionally, it may be advantageous to conduct said alkylation under an inert atmosphere such as, for example, oxygen-free argon or nitrogen gas.

The compounds of formula (I-a) can also be prepared by alkylating an appropriate bicyclic derivative of formula (V-a) or a salt thereof, with an alkylating reagent of formula (IV-a) following art-known N-alkylation procedures. In formula (IV-a) $W^2$ represents a reactive leaving group such as, for example halo, e.g. chloro, bromo or iodo, a sulfonyloxy-group, e.g. methanesulfonyloxy, trifluoromethanesulfonyloxy, benzenesulfonyloxy, 4-methylbenzenesulfonyloxy, naphthalenesulfonyloxy and the like reactive leaving groups.

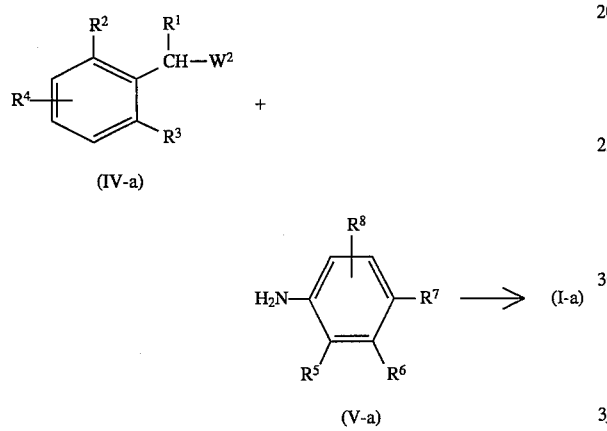

Said N-alkylation reaction can conveniently be carried out by stirring the reactants, optionally in a reaction-inert solvent such as, for example, an aromatic solvent, e.g. benzene, methylbenzene, dimethylbenzene, chlorobenzene, methoxybenzene and the like; a ketone, e.g. 2-propanone, 4-methyl-2-pentanone and the like; an ether, e.g. 1,1'-oxybisethane, tetrahydrofuran, 1,4-dioxane and the like; a dipolar aprotic solvent, e.g. N,N-dimethylformamide, N,N-dimethylacetamide, dimethylsulfoxide, pyridine, acetonitrile and the like; or a mixture of such solvents.

An appropriate base such as, for example, an alkali metal or an earth alkaline metal carbonate, hydrogen carbonate, hydroxide, oxide, carboxylate, alkoxide, hydride or amide, e.g. sodium carbonate, sodium hydrogen carbonate, potassium carbonate, sodium hydroxide, calcium oxide, sodium acetate, sodium methoxide and the like, or an organic base such as, for example, an amine, e.g. N,N-diethylethanamine, N-(1-methylethyl)-2-propanamine, 4-ethylmorpholine, 1,4-diazabicyclo[2.2.2]octane, pyridine and the like, may optionally be used to pick up the acid which is formed during the course of the reaction. Additionally, it may be advantageous to conduct said alkylation under an inert atmosphere such as, for example, oxygen-free argon or nitrogen gas.

In an efficient alternative for the foregoing N-alkylation reactions one of the reactants is used as a solvent and the reaction is conducted by heating and stirring this reaction mixture at an elevated temperature.

The compounds of formula (I-b) can be prepared in a similar manner by reacting an intermediate of formula (V-b) or a salt thereof, with an alkylating reagent (IV-b) wherein $W^2$ is as defined under formula (IV-a).

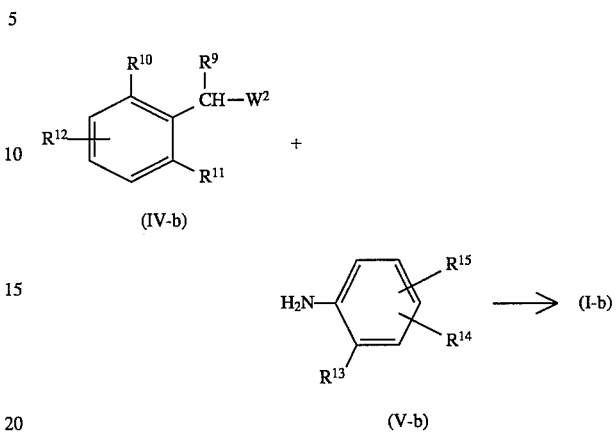

The compounds of formula (I-a) wherein $R^1$ is a radical of formula $-C(=X)NH^2$, said compounds being represented by formula (I-a-1) when X is O and by formula (I-a-2) when X is S, can be prepared by reacting a nitrile of formula (VI-a), with a reagent H2X (VII), namely water or hydrogen sulfide, under appropriate conditions.

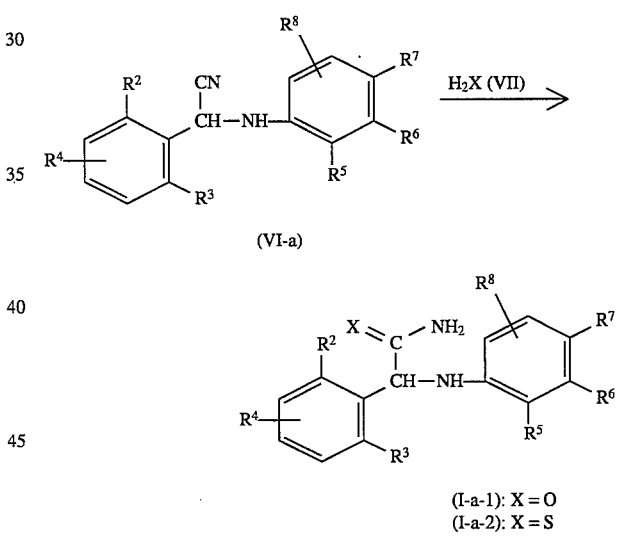

(I-a-1): X = O
(I-a-2): X = S

The hydrolysis of the nitrile of formula (VI-a) to the corresponding amide of formula (I-a-1), can easily be carried out following art-known procedures. Preferably said hydrolysis is carded out at room temperature or low temperatures such as, for example, between 0° C. and room temperature, in a concentrated strong acid, e.g. concentrated sulfuric acid, hydrochloric acid, hydrobromic acid and the like, optionally in the presence of a small amount of water; or by stirring the nitrile of formula (VI-a) in a carboxylic acid, e.g. formic acid and the like, while bubbling hydrochloric acid through the reaction mixture.

The nitrile (VI-a) can conveniently be converted into the thioamide (I-a-2) by reaction with hydrogen sulfide in an appropriate solvent, e.g. pyridine, a mono-, di- or trimethylated pyridine and the like solvents, and in the presence of an appropriate base such as an amine, e.g. N,N-diethylethanamine, N-methylmorpholine, N-(1-methyl-ethyl)-2-propanamine and the like. This latter reaction can conveniently be conducted at room temperature and in some instances even at lower temperatures such as, for example, between about 0° C. and room temperature. The thioamide compounds of formula (I-a-2) can conveniently be converted into the corresponding amides of formula (I-a-1) by reaction with an oxidizing reagent such as, for example, hydrogen peroxide in water, optionally in admixture with an organic co-solvent.

The compounds of formula (I-a) wherein $R^1$ is a radical $-C(=O)NR^{16}R^{17}$, $R^{16}$ and $R^{17}$ each independently being hydrogen or $C_{1-4}$alkyl; said compounds being represented by formula (I-a-3) can be prepared by reacting an aminoacid or a derivative thereof of formula (VIII-a), with an appropriate amine (IX).

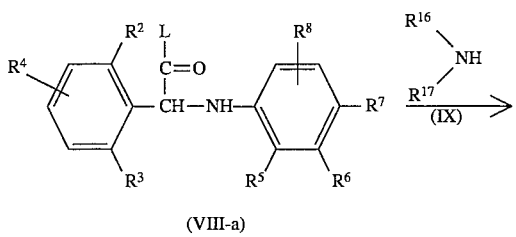

(VIII-a)

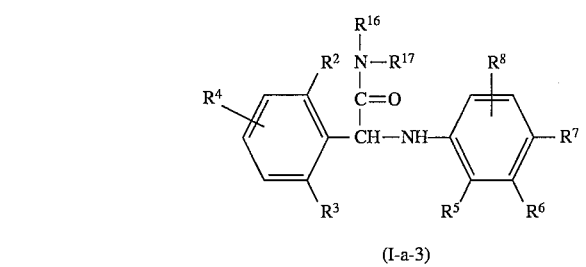

(I-a-3)

Said preparation of the amides of formula (I-a-3) can conveniently be carded out following art-known amidation and transamidation reactions. For example, said amides can be prepared by reacting an appropriate carboxylic acid (L is OH) with an amine (IX) in the presence of a reagent capable of promoting amidation reactions. Typical examples of such reagents are for example, dicyclohexylcarbodiimide, 2-chloro-1-methylpyridinium iodide, phosphorus pentoxide, 1,1'-carbonylbis[1H-imidazole], 1,1'-sulfonyl-bis[1H-imidazole] and the like reagents.

Alternatively, said carboxylic acids may be convened into a suitable reactive functional derivative thereof such as, for example, an acyl halide, symmetric or mixed anhydride, ester, amide, acyl azide and the like derivatives, before reaction with the amine of formula (IX). Said reactive functional derivatives may be prepared following art known methods, for example, by reacting the carboxylic acid with a halogenating reagent such as, for example, thionyl chloride, phosphorous trichloride, polyphosphorous acid, phosphoryl chloride, oxalyl chloride and the like, or by reacting said carboxylic acid with an acyl halide such as acetyl chloride, ethyl chloroformate and the like.

The compounds of formula (I-a), wherein $R^1$ is $C_{3-6}$cycloalkyl or $C_{1-4}$alkyl, said radicals being represented by R la and said compounds being represented by formula (I-a-4), can be prepared by reacting an organometallic reagent of formula (XI-a) wherein $R^{1a}$ represents $C_{3-6}$cycloalkyl or $C_{1-4}$alkyl, and M represents a metal group, such as, for example, lithium, halomagnesium, copperlithium, with an imine of formula (X-a), following art-known methodologies.

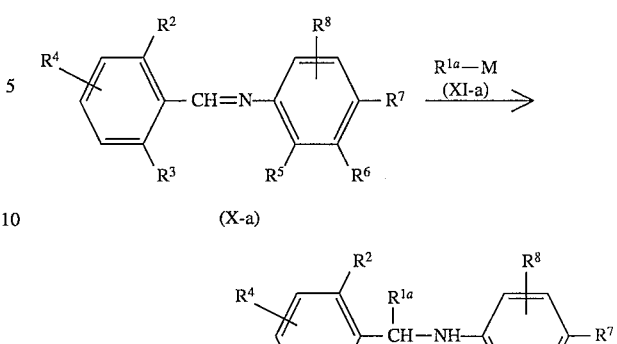

In an analogous way the compounds of formula (I-b) wherein, $R^9$ is $C_{3-6}$cycloalkyl or $C_{1-4}$alkyl, said radicals being represented by $R^{9a}$ and said compounds being represented by formula (I-b-4), can be prepared by reacting an organometallic reagent of formula (XI-b), wherein M represents a metal group, such as, for example, lithium, halomagnesium, copperlithium, with an imine of formula (X-b). It may be necessary in the above addition reactions to protect certain functional groups of certain substituents in the imines of formula (X-a) and (X-b) prior to the addition reaction.

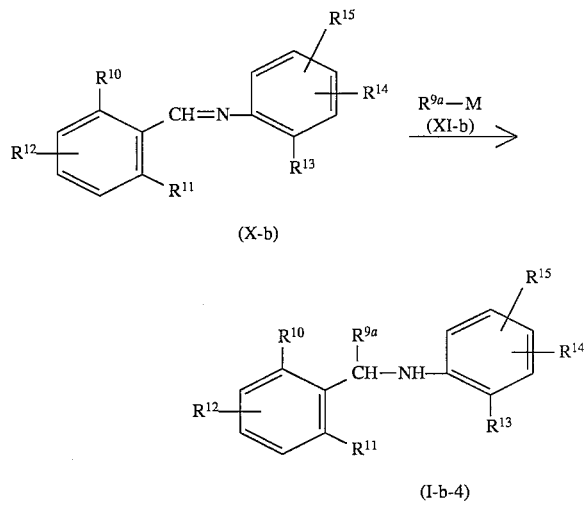

The compounds of formula (I-a) or (I-b) wherein $R^5$, $R^6$, $R^7$, $R^9$ or $R^{13}$ represent $C_{1-6}$alkyl—$C(=Y)$, wherein Y represents O, can be prepared by hydrolysing the corresponding acetal or ketal.

The compounds of formula (I-a), respectively the compounds of formula (I-b) can be converted into one another following an-known functional group transformation reactions. For example, the compounds wherein $R^5$, $R^6$, $R^7$, $R^8$ or $R^{13}$ represent a radical $C_{1-6}$alkyl—$C(=Z)$— wherein Z represents N—OH, N—OCH$_3$, N—NH$_2$ or N—N(CH$_3$)$_2$, can be prepared following art-known procedures from the corresponding compounds wherein Z represents O by reaction with hydroxylamine, O-methyl-hydroxylamine, hydrazine or di(methyl)hydrazine or a suitable addition salt form thereof.

The carbonyl group of the compounds of formula (I-a) wherein $R^5$ and $R^6$ taken together form a bivalent radical —C(=O)(CH$_2$)$_2$—, —C(=O)(CH$_2$)$_3$—, —C(=O)(CH$_2$)$_2$—O—, —C(=O)CH$_2$—O— or —C(=O)(CH$_2$)$_2$—NH—, can be convened into a methylene group following art-known reduction procedures such as, for example, by reaction with zinc-amalgam in an acid such as hydrochloric acid.

The compounds of this invention have at least one asymmetric carbon atom in their structure, namely the carbon atom bearing the $R^1$ respectively the $R^9$ group. Said chiral center and any other chiral center which may be present, can be indicated by the stereochemical descriptors R and S.

Pure stereochemically isomeric forms of the compounds of formula (I) may be obtained by the application of an-known procedures. Diastereoisomers may be separated by physical methods such as selective crystallization and chromatographic techniques, e.g. counter current distribution, liquid chromatography and the like. Pure stereochemically isomeric forms may also be derived from the corresponding pure stereochemically isomeric forms of the appropriate starting materials, provided that the reactions occur stereospecifically. Preferably, if a specific stereoisomer is desired, said compound will be synthesized by stereospecific methods of preparation. These methods will advantageously employ enantiomerically pure starting materials. Stereochemically isomeric forms of the compounds of formula (I) are obviously intended to be included within the scope of the invention.

The compounds of formula (I) as prepared in the above described processes are generally racemic mixtures of enantiomers which can be separated from one another following an-known resolution procedures. The racemic compounds of formula (I) which are sufficiently basic may be converted into the corresponding diastereomeric salt forms by reaction with a suitable chiral acid. Said diastereomeric salt forms are subsequently separated, for example, by selective or fractional crystallization and the enantiomers are liberated therefrom by alkaline or acidic hydrolysis.

An interesting manner of separating the enantiomeric forms of the compounds of formula (I) involves liquid chromatography using a chiral stationary phase such as suitably derivatized cellulose, for example, tri(dimethylcarbamoyl)cellulose (Chiracel OD®) and similar chiral stationary phases.

As an alternative to the above-mentioned resolution of the compounds of formula (I), there should be mentioned also the resolution of racemic intermediates. Particularly useful intermediates for this purpose are the aminoacid derivatives of formula (VIII-a) wherein L is hydroxy, said intermediates being represented by formula (VIII-a-1).

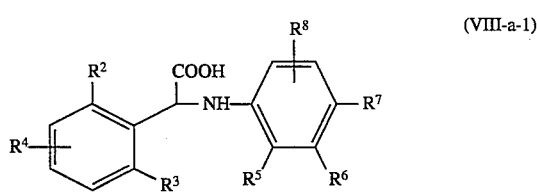

(VIII-a-1)

The aminoacids of formula (VIII-a-1) can conveniently be resolved by formation of the corresponding diastereomeric salt forms by reaction with a suitable chiral base such as phenylethanamine, naphthylethanamine, cinchonine and other alkaloid bases. Obviously, said aminoacids may also be resolved by liquid chromatography using an appropriate chiral stationary phase.

The enantiomeric forms of the aminoacids of formula (VIII-a-1) are converted into the enantiomeric forms of the compounds of formula (I-a) according to the procedures described hereinbefore for converting the intermediates of formula (VIII-a) into the compounds of formula (I-a).

A number of the intermediates and starting materials employed in the foregoing preparations are known compounds which can be prepared according to art-known methodologies of preparing said or similar compounds. Some intermediates are less common or are novel, and a number of preparation methods will therefore be described hereinafter in more detail.

The intermediates of formula (VI-a), can be prepared by reacting an appropriate benzaldehyde (XII-a) with a bicyclic amino intermediate of formula (V-a) in the presence of a cyanide salt and a suitable solvent.

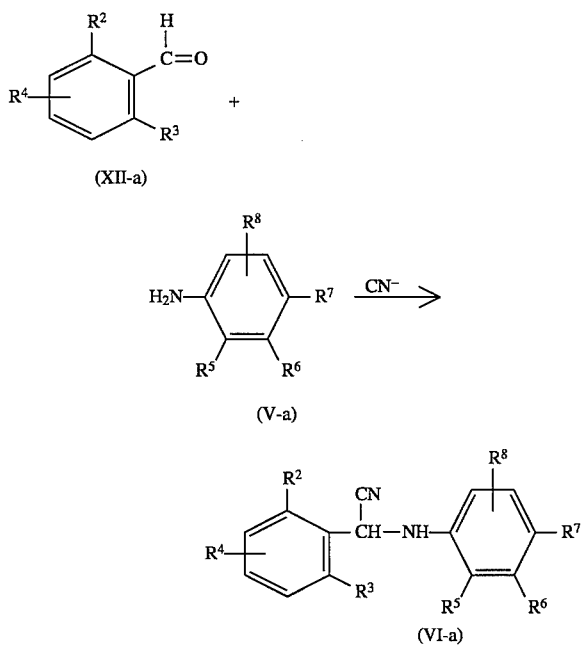

As examples of cyanide salts there may be mentioned alkali metal and earth alkaline metal cyanides, e.g., sodium and potassium cyanide. Suitable solvents comprise, for example, water; alkanols, e.g. methanol, ethanol and the like, carboxylic acids, e.g. acetic acid, particularly glacial acetic acid, propanoic acid and the like; or a mixture of such solvents. Said reaction is conveniently carded out by stirring at room temperature and, if desired, slightly heating the reactants, for example between 40° C. and 60° C., in particular at about 50° C. In some instances it is advantageous to carry out said reaction in the presence of a metal salt such as, for example, anhydrous zinc chloride and the like, in a non-aqueous solvent, particularly glacial acetic acid, as described in Chem. Ber., 98, 3902 (1965).

Alternatively, an intermediate imine of formula (X-a) formed by reacting an aldehyde of formula (XI-a) with an amine of formula (V-a) following art-known procedures, is reacted with trimethylsilylcyanide, in an appropriate solvent such as, for example, a halogenated hydrocarbon, e.g. trichloromethane in the presence of a suitable Lewis acid catalyst, e.g. zinc iodide.

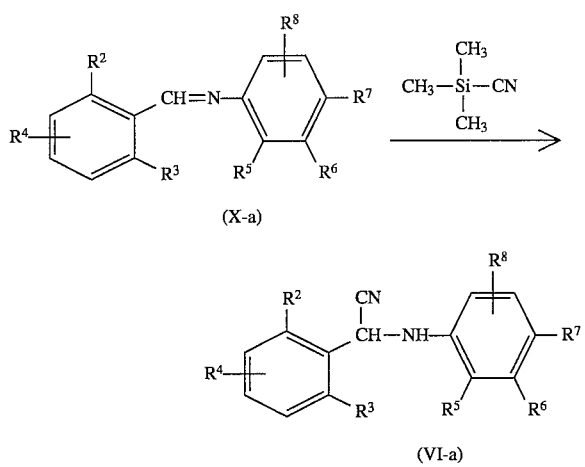

(X-a)

(VI-a)

The aniline derivatives of formula (V-a) wherein $R^5$ and $R^6$ are taken together to form a bivalent radical of formula, —(C=O)—(CH$_2$)$_2$—, —(C=O)—(CH$_2$)$_3$—, —(C=O)CH$_2$—O—, (C=O)CH$_2$—NH—, —(C=O)—(CH$_2$)$_2$—O—, said radicals being represented by —(C=O)—T— and said derivatives being represented by formula (V-a-1), can be prepared by cyclizing an intermediate of formula (XIII) wherein $R^{21}$ is C$_{1-4}$alkyl, preferably methyl or ethyl, and wherein L is hydroxy, halo or alkylcarbonyloxy, with formation of intermediate (XIV) and subsequent deprotection.

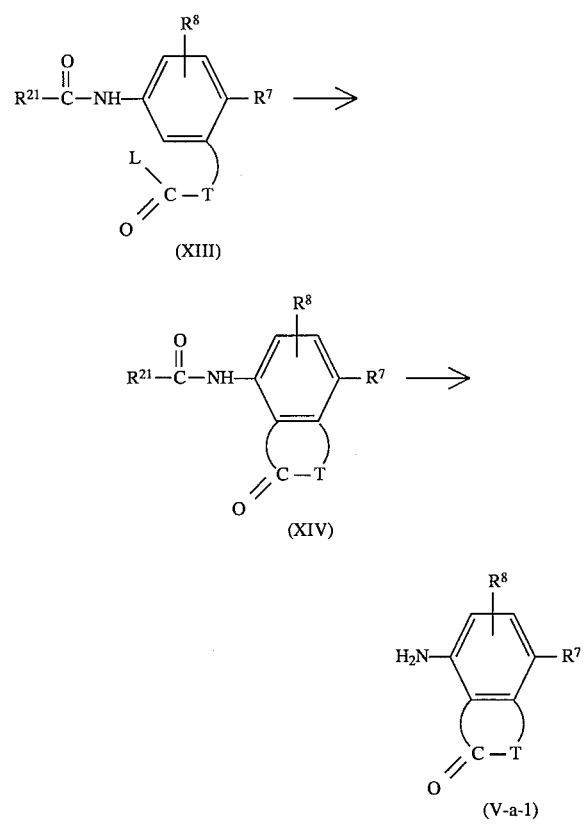

Said cyclization can be performed by reacting the amides of formula (XIII), wherein L is halo or alkylcarbonyloxy, with a Lewis acid and such as, for example aluminum chloride, ferric chloride, zinc chloride and the like in a reaction-inert solvent such as carbondisulfide and the like, or by reacting the amides of formula (XIII), wherein L is OH, with an acid such as for example polyphosphoric acid, sulfuric acid and the like. Said deprotection can be performed following art-known procedures to hydrolyze amides and may ensue during aqueous work-up of the reaction mixture.

The aniline derivatives of formula (V-a) and (V-b) can be prepared by reducing nitrobenzene derivatives following art-known procedures.

Acylation of said aniline derivatives can be performed by reacting a protected aniline derivative, preferably as an amid, with acylating reagent, such as for example, an acid, e.g. acetic acid, propanoic acid, butanoic acid in the presence of polyphosphoric acid, sulfuric acid and the like; or an acid derivative such as an acyl halide or an acid anhydride and the like in the presence of a Lewis acid such as aluminum chloride, ferric chloride and the like. An interesting alternative for said acylation is reacting a benzene derivative with a nitrile in the presence of a Lewis acid such as for example boron trichloride and subsequent hydrolysis of the intermediate imine.

The compounds of formula (I) show antiretroviral properties, in particular against Human Immunodeficiency Virus (HIV), also known as LAV, HTLV-III or ARV, which is the etiological agent of Acquired Immune Deficiency Syndrome (AIDS) in humans. The HIV virus preferentially infects human T-4 cells and destroys them or changes their normal function, particularly the coordination of the immune system. As a result, an infected patient has an everdecreasing number of T-4 cells, which moreover behave abnormally. Hence, the immunological defense system is unable to combat infections and neoplasms and the HIV infected subject usually dies by opportunistic infections such as pneumonia, or by cancers. Other conditions associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC).

Due to their antiretroviral properties, particularly their anti-HIV and especially their anti-HIV-1 properties, the compounds of formula (I), their pharmaceutically acceptable salts and the stereochemically isomeric forms thereof, are useful in the treatment of individuals infected by HIV and for the prophylaxis of individuals. In general, the compounds of the present invention may be useful in the treatment of warm-blooded animals infected with viruses whose existence is mediated by, or depends upon, the enzyme reverse transcriptase. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic CNS diseases caused by retroviruses, such as, for example HIV mediated dementia and multiple sclerosis.

Additionally, it has been found that also the intermediates of formula (VI-a) show antiretroviral properties, in particular against HIV and especially against HIV-1.

The subject compounds may be formulated into various pharmaceutical forms for administration purposes. As appropriate compositions there may be cited all compositions usually employed for systemically or topically administering drugs. To prepare the pharmaceutical compositions of this invention, an effective amount of the particular compound, optionally in acid-addition salt form, as the active ingredient is combined in intimate admixture with a pharmaceutically acceptable carder, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules, and tablets. Because of their ease in administration, tablets and capsules represents the most advantageous oral dosage unit form, in which case solid pharmaceutical carriers are obviously employed. For parenteral compositions, the carrier will usually comprise sterile water, at least in large pan, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are-intended to be convened, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. As appropriate compositions for topical application them may be cited all compositions usually employed for topically administering drugs, e.g., creams, gellies, dressings, shampoos, tinctures, pastes, ointments, salves, powders and the like. Application of said compositions may be by aerosol e.g. with a propellent such as nitrogen, carbon dioxide, a freon, or without a propellent such as a pump spray, drops, lotions, or a semisolid such as a thickened composition which can be applied by a swab. In particular compositions, semisolid compositions such as salves, creams, gellies, ointments and the like will conveniently be used.

It is especially advantageous to formulate the aforementioned pharmaceutical compositions in dosage unit form for ease of administration and uniformity of dosage. Dosage unit form as used herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions and the like, and segregated multiples thereof.

Those of skill in the treatment of HIV-infection could easily determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

It is evident that said effective daily amount may be lowered or increased depending on the response of the treated subject and/or depending on the evaluation of the physician prescribing the compounds of the instant invention. The effective daily amount ranges mentioned hereinabove are therefore guidelines only and are not intended to limit the scope or use of the invention to any extent.

The following examples are intended to illustrate and not to limit the scope of the present invention.

EXPERIMENTAL PART

A. Preparation of the Intermediates

Example 1 a) To a stirred mixture of 10.5 g of N-(2,3-dihydro-1H-inden-5-yl)acetamide and 4.7 ml of acetyl chloride in 100 ml of carbondisulfide were added portionwise 17.3 g of aluminum chloride at room temperature. After stirring for 2 hours at reflux temperature, the cooled reaction mixture was poured into 50 ml ice/HCl. The separated aqueous layer was extracted with dichloromethane. The extract was combined with the former organic layer, washed with water, dried, filtered and evaporated. The residue was purified by column chromatography (silica gel; dichloromethane/methanol 99:1 ). The eluent of the desired fraction was evaporated and the residue was crystallized from 2,2'-oxybispropane. The crystallized product was filtered off and dried, yielding 6.3 g (48.3%) of N-(6-acetyl-2,3-dihydro- 1H-inden-5-yl)acetamide (interm. 1).

b) A solution of 6.3 g of intermediate (1) in 75 ml of a hydrochloric acid solution 5N was refluxed for 45 minutes. After cooling, the reaction mixture was treated with ammonia. The precipitated product was filtered off, washed with water and dissolved in dichloromethane. After washing with water, the separated organic layer was dried, filtered and evaporated, yielding 4.2 g (82.7%) of 1-(6-amino-2,3-dihydro-1H-inden-5-yl)ethanone (interm. 2 ).

Example 2 a) To a stirred and cooled mixture of 32 ml of sulfuric acid and 14 ml of water there were added 17 g of 2,3-dihydro-5-chlorobenzofuran, while keeping the temperature at 25° C. After cooling to 0° C. there were added dropwise 14 ml of nitric acid. Stirring and cooling at 0° C. was continued for 44 hours. The reaction mixture was diluted with water (temp. <10° C.) and stirred for 15 min. The precipitate was filtered off, washed with water and recrystallized from a mixture of ethyl acetate and hexane (30:70), yielding 8.9 g (40.5%) of 5-chloro-2,3-dihydro-7-nitrobenzofuran (interm. 3).

b) A mixture of 4.0 g of intermediate (3), 1 ml of a solution of thiophene in methanol 4%, and 150 ml of methanol was hydrogenated for 2 hours at normal pressure and room temperature in the presence of 2 g of platinum-on-charcoal catalyst 5%. The catalyst was filtered off over diatomaceous earth and washed with methanol. The combined filtrates were evaporated and the residue was purified by column chromatography (silica gel; ethyl acetate/n.hexane 15:85). The eluent of the desired fraction was evaporated, yielding 2.7 g (79.6%) of 5-chloro-2,3-dihydro-7-benzofuranamine (interm. 4).

Example 3 a) A mixture of 129 g of 2-chloro-1,3-dimethyl-5-nitrobenzene, 125 g of 1-bromo-2,5-pyrrolidinedione, 12 g of dibenzoyl peroxide and 1200 ml of tetrachloromethane was stirred for 2 hours at reflux temperature using a water separator. Twice there was added an extra portion of 20 g of dibenzoyl peroxide during a refluxing period of 29 hours. After cooling, the reaction mixture was washed with water, dried, filtered and evaporated. The residue was purified by column chromatography (silica gel; $CH_2Cl_2$/hexane 50:50). The eluent of the desired fraction was evaporated, yielding 130 g (70.2%) of 1-(bromomethyl)-2-chloro-3-methyl-5-nitrobenzene (interm. 5).

b) To a solution of 116 g of triethyl methanetricarboxylate in 750 ml of N,N-dimethylformamide there were added portionwise 24 g of sodium hydride under a nitrogen atmosphere. After stirring for 1 hour at room temperature, there was added dropwise a solution of 130 g of intermediate (9) in 300 ml of N,N-dimethylformamide. Stirring at room temperature was continued overnight. The reaction mixture was evaporated and the residue was partitioned between water and dichloromethane. The aqueous layer was separated and re-extracted with dichloromethane (2x). The combined organic layers were washed with 5% $Na_2CO_3$ (aq.) and water, dried, filtered and evaporated. The residue was purified by column chromatography (silica gel; $CH_2Cl_2$/hexane 80:20). The eluent of the desired fraction was evaporated, yielding 102 g (49.1%) of triethyl 2-(2-chloro-3-methyl-5-nitrophenyl)-1,1,1-ethanetricarboxylate (interm. 6).

c) A mixture of 102 g of intermediate (6), 1000 ml of acetic acid and 1000 ml of sulfuric acid was stirred for 3 hours at reflux temperature. After cooling, the reaction mixture was poured into ice-water and the whole was stirred for 1 hour. The precipitate was filtered off (*), recrystallized from 2,2'-oxybispropane and dried in vacuo at 70° C., yielding 28 g (46.9%) of product. The aqueous layer of the flitrate(*) was extracted with dichloromethane (2x). The combined extracts were dried, filtered and evaporated and the residue was dissolved in 2,2'-oxybispropane. This solution was extracted with NaOH 5% and the extract was acidified with HCl. The precipitate was filtered off and dried in vacuo at 70° C., yielding an additional 16 g (26.8%) of product. Total yield: 44 g (73.7 %) of 2-chloro-3-methyl-5-nitrobenzenepropanoic acid (interm. 7).

d) A mixture of 28 g of intermediate (7), 400 ml of acetic acid, 5 ml of a solution of thiophene in methanol 4 % and 50 ml of acetic anhydride was hydrogenated at normal pressure and room temperature in the presence of 5 g of platinum-on-charcoal catalyst 10%. After the calculated amount of hydrogen was taken up, the catalyst was filtered off and the filtrate was evaporated. The residue was co-evaporated with methylbenzene (2x), yielding 28 g (95.2%) of 5-(acetylamino)-2-chloro-3-methylbenzenepropanoic acid (interm. 8).

e) A mixture of 28 g of intermediate (8) and 200 g of polyphosphoric acid was stirred for ½ hour at 120° C. The warm reaction mixture was poured into water. The precipitate was filtered off and dissolved in a mixture of dichloromethane and methanol. This solution was washed with water, dried, filtered and evaporated. The residue was purified by column chromatography (silica gel; $CH_2Cl_2$/$CH_3OH$ 99:1 ). The eluent of the desired fraction was evaporated, yielding 6.7 g (24.5%) of N-(7-chloro-2,3-dihydro- 6-methyl-3-oxo-1H-inden-4-yl)acetamide (interm. 9).

f) A mixture of 7.6 g of intermediate (9), 2 ml of a solution of thiophene in methanol 4%, 8 g of calciumoxide, 250 ml of methanol and 250 ml of tetrahydrofuran was hydrogenated at normal pressure and 50° C. in the presence of 4 g of palladium-on-charcoal catalyst 10%. After the calculated amount of hydrogen was taken up, the catalyst was filtered off and the filtrate was evaporated. The residue was successively crystallized from 2,2'-oxybispropane and from acetonitrile. The product was filtered off and dried in vacuo at 70° C. yielding 3 g (46.1% ) of product. Evaporation of the mother liquors yielded an additional 2.6 g (40.0%) N-(2,3-dihydro-6-methyl-3-oxo-1H-inden-4-yl)acetamide (interm. 10).

g) A mixture of 3 g of intermediate (10) and 50 ml of HC15N was stirred for 1 hour at reflux temperature. After cooling, the reaction mixture was basified with ammonia. The product was extracted with dichloromethane (2x) and the combined extracts were dried, filtered and evaporated, yielding 1.2 g (49.6%) of 7-amino-2,3-dihydro-5-methyl-1H-inden-1-one (interm. 11 ).

Example 4 a) 1,2-dichloroethane (70ml) was stirred and cooled to 0°–5° C. under nitrogen flow. Boron trichloride (0.06 tool) was allowed to bubble through 1,2-dichloroethane for 30 minutes. A solution of 2-chloro-5-methoxybenzenamine (0.055 mol) in 1,2-dichloroethane (20 ml) was added dropwise at <5° C. The reaction mixture was stirred for 15 minutes at <15° C. (suspension). 2-chloroacetonitrile (0.13 tool) was added dropwise at <5° C. The resulting mixture was added dropwise to a solution of aluminium chloride (0.06 tool) in 1,2-dichloroethane (20 ml), which was stirred at 5° C. Upon complete addition at 5°–10° C., the reaction mixture was stirred for 30 minutes at room temperature. Then, the reaction mixture was stirred and refluxed for 3 hours. The reaction mixture was cooled. HC12N (220 ml) was added dropwise, while the mixture was cooled on an ice bath (temperature rise to 30° C., precipitation occurred). Water (50 ml) and 1,2-dichloroethane (20 ml) were added. The reaction mixture was warmed to 80° C. and stirred at this temperature for 30 minutes. The organic layer was separated. The aqueous layer was extracted with 1,2-dichloroethane (2×50 ml). The organic layer was separated, combined with the previous organic phase, washed with water, dried ($MgSO_4$), filtered and the solvent was evaporated. The residue was suspended in hexane, filtered off and dried (vacuum; 60° C.), yielding 11.6 g 1-(2-amino-3-chloro-6-methoxyphenyl)-2-chloroethanone (90% impure product). A sample (3 g) was recrystallized from 2,2'-oxybispropane. The crystals were filtered off and dried (vacuum; 60° C.), yielding 1.6 g (48%) of 1-(2-amino-3-chloro-6-methoxyphenyl)- 2-chloroethano mp. 111.9° C. (interm. 12).

b) Aluminium chloride (0.82 tool) was suspended in $CH_2Cl_2$ (425 ml). Intermediate (12) (0.27 mol) in $CH_2Cl_2$ (500 ml) was added dropwise (temperature raised till 30° C.) and the mixture was stirred and refluxed for 6 hours. The mixture was cooled, decomposed with HC12N (11) and $CH_2Cl_2$ and $CH_3OH$ were added. The organic layer was separated and the aqueous layer was extracted with $CH_2Cl_2$. The combined organic layers were dried ($MgSO_4$), filtered off and evaporated. The residue was purified by column chromatography over silica gel (eluent: hexane/ethyl acetate 50/50). The pure fractions were collected and evaporated, yielding 20 g of fraction 1 and 10 g fraction 2 (total: 60%). A sample (10g) from fraction 1 was boiled up in $CH_3OH$ and N,N-diethylethanamine was added. The mixture was cooled to 0° C. and filtered off. The precipitate was crystallized from $CH_3OH$, cooled to 0° C., filtered off and dried in vacuo at 40° C., yielding 7.4 g (44.8%) 4-amino-5-chloro-3(2H)-benzofuranone; mp. 160.0° C. (interm. 13).

c) A mixture of intermediate (13) (0.087 mol) and potassium acetate (10 g) in methanol (250 ml) was hydrogenareal at 50° C. with palladium-on-charcoal (5 g) as a catalyst in the presence of thiophene (0.5 ml). After uptake of hydrogen (1 equiv), the catalyst was filtered off and the tiltrate was evaporated. The residue was purified by column chromatography over silica gel (eluent: $CH_2Cl_2$). The pure fractions were collected and the solvent was evaporated, yielding 8.4 g (65%) of 4-amino-3(2H)-benzofuranone (interm. 14).

d) A mixture of intermediate (14) (0.01 mol) and 2,6-dichloro-benzaldehyde (0.01 mol) in methylbenzene (100 ml) was stirred and refluxed for 20 hours, using a water-separator. The reaction mixture was cooled and the solvent was evaporated. The residue was stirred in boiling 2,2'-oxybixpropane, cooled and the resulting precipitate was filtered off, stirred in boiling 2-propanol, cooled, filtered off and dried (vacuum; 70° C.), yielding 1.8 g (60%) of product. A sample (1g) was stirred in boiling $CH_3CN$, filtered while still warm and dried (vacuum; 70° C.), yielding 0.5 g (29.4%) of 4-[[( 2,6-dichlorophenyl)methylene]amino]-3(2H)-benzofuranone (interm. 15). In a similar manner was also prepared: 7-[[(2,6-dichlorophenyl)methylenelamino]- 1 (3H)-isobenzofuranone (interm. 16).

Example 5

A solution of 3.5 g of intermediate (2) and 4.72 g of 2,6-dichlorobenzaldehyde in 100 ml of acetic acid was stirred for 2 hours at room temperature. 1.75 g of potassium cyanide was added and after stirring for 20 hours at room temperature, the reaction mixture was poured into water. The precipitated product was filtered off, washed with water and recrystallized from 2-propanol. The product was filtered off and dried, yielding 6 g (83.5%) of (±)-α-[(6-acetyl-2,3-dihydro-1H-inden-5-yl)amino]- 2,6-dichlorobenzeneacetonitrile (interm. 17).

Example 6

A mixture of 15.3 g of 2,6-dichlorobenzaldehyde, 10 g of 8-quinolinamine, 175 ml of acetic acid and 16.7 g of zinc(II)chloride was stirred for 1 hour at room temperature. There were added 7 g of potassium cyanide and stirring at room temperature was continued for 4 hours. The precipitate was filtered off* and dissolved in dichloromethane. Unsoluble product was filtered off* and stirred for 24 hours at 60° C. in 300 ml of acetic acid together with 7 g of potassium cyanide. A first product fraction of 4.6 g (20.2%) was obtained. The filtrate* was washed with water, dried, filtered and evaporated. The residue was successively triturated in 2,2'-oxybispropane and recrystallized from acetonitrile, yielding an additional product fraction of 0.9 g (3.9%). Total yield: 5.5 g (24.1%) of 2,6-dichloro-α-(8-quinolinylamino) benzeneacetonitrile; mp. 160.6° C. (interm. 18).

Example 7

A mixture of intermediate (15) (0.0043 tool), trimethylsilanecarbonitrile (0.065 mol) and zinc iodide (catalytic amount) in trichloromethane (20 ml) was stirred for 20 hours at room temperature. Extra trimethylsilanecarbonitfile (1.1 ml) was added. Extra zinc iodide (catalytic amount) was added. The reaction mixture was stirred at room temperature for the week-end. The reaction mixture was poured out into water. The layers were separated. The aqueous layer was extracted with $CH_2Cl_2$. The organic layer was separated, dried ($MgSO_4$), filtered and the solvent was evaporated. The residue was purified by column chromatography over silica gel (eluent: $CH_2Cl_2$/hexane 7/3). Two desired fractions were collected and the solvent was evaporated. The first column fraction (0.3 g) was stirred in boiling 2,2'-oxybispropane, filtered off and dried (vacuum; 70° C.), yielding 0.25 g (18%) of (±)-2,6-dichloro-α-[(2,3-dihydro-3-oxo- 4-benzofuranyl)amino]benzeneacetonitrile.

The following intermediates of formula (VI-a) were prepared:

| Interm. No. | Ex. No. | $R^5$, $R^6$, $R^7$, $R^8$ | physical data |
|---|---|---|---|
| 17 | 5 | (6-acetyl-2,3-dihydro-1H-inden-5-yl) | — |
| 18 | 6 | 8-quinolinyl | mp. 160.6° C. |
| 19 | 7 | (2,3-dihydro-3-oxo-4-benzofuranyl) | mp. 161.9° C. |

-continued

| Interm. No. | Ex. No. | R⁵ structure | physical data |
|---|---|---|---|
| 20 | 6 | 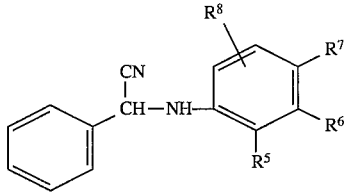 | — |
| 21 | 5 | 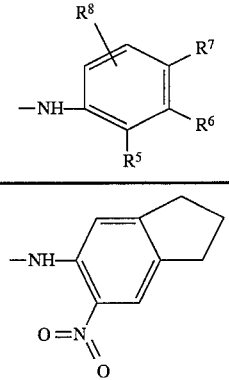 | mp. 79.5° C. |
| 22 | 5 | 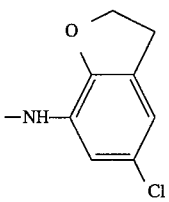 | — |
| 23 | 5 | 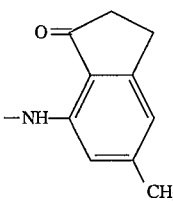 | mp. 133.0° C. |
| 24 | 5 | 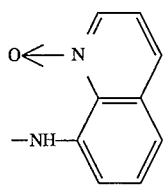 | mp. 184.0° C. |
| 25 | 5 | 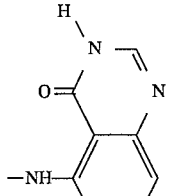 | mp. 256.3° C. |

-continued

| Interm. No. | Ex. No. | R⁵ structure | physical data |
|---|---|---|---|
| 26 | 6 | 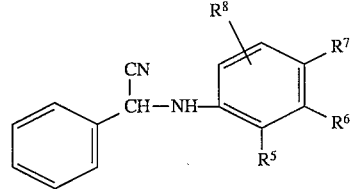 | mp. 208.4° C. |

Example 8 a) 2-methyl-2-(2-nitrophenyl)- 1,3-dioxolane (0.132 mol) was dissolved in tetrahydrofuran (600 ml) and this solution was hydrogenated with platinum on activated carbon (4 g) as a catalyst in the presence of calcium oxide (10 g) and thiophene (3 ml). After uptake of $H_2$ (3 equiv), the catalyst was filtered on celite and washed with tetrahydrofuran. The flitrate was evaporated. The residue was recrystallized from n-hexane. The crystals were filtered off and dried, yielding 18.5g (78%) of 2-(2-methyl-1,3-dioxolan-2-yl)benzenamine (interm. 27).

b) A solution of 2,6-dichlorobenzaldehyde (0.028 mol) and intermediate (27) (0.028mol) in methylbenzene (100 ml) was stirred and refluxed for 24 hours, using a Dean-Stark water separator. The solvent was evaporated. The residue crystallized upon standing. The crystals were filtered off and dried, yielding N-[(2,6-dichlorophenyl)-methylene]-2-(2-methyl-1,3-dioxolan-2-yl)benzenamine (interm. 28).

c) Reaction performed under $N_2$ flow. A solution of bromocyclopropane (0.064 mol) in 1,1'-oxybisethane (48 ml) was added dropwise to a suspension of lithium (0.12 mol) in 1,1'-oxybisethane (48 ml;dry), stirred at 0° C. The reaction mixture was stirred for 90 minutes at 4°–5° C. (ice-bath). A solution of intermediate (28) (0.048mol) in 1,1'-oxybisethane (48 ml) was added (exothermic temperature rise). The reaction mixture was stirred for 3 hours at room temperature. The reaction mixture was cooled. Water was added. The organic layer was separated. The aqueous layer was extracted with $CH_2Cl_2$. The organic layer was separated, combined with previous organic phase, dried ($MgSO_4$), filtered and the solvent was evaporated. The residue was purified twice by column chromatography over silica gel (eluent: $CH_2Cl_2$/hexane 50/50). The pure fractions were collected and the solvent was evaporated. The residue was triturated in 2,2'-oxybispropane. The solid was filtered off and dried, yielding 4.8g (26.5%) of (±)-2,6-dichloro-a-cyclopropyl-N-[2-(2-methyl- 1,3-dioxolan-2-yl)phenyl]benzenemethanamine; mp. 150.7° C. (interm. 29).

Note: At the top of both columns the generic structures are shown:

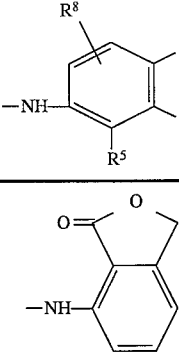

B. Preparation of the Final Compounds

Example 9

2.2 g of intermediate (23) was dissolved in 50 ml of formic acid. HCl was allowed to bubble through this solution for 15 min. The reaction mixture was stirred at room temperature for 1 hour. The reaction mixture was poured out into water and the resulting precipitate was filtered off, and crystallized for acetonitrile. The crystals were filtered off and dried in vacuo at 70° C., yielding 0.4 g (19%) of (±)-2,6-dichloro-α-[(2,3-dihydro- 6-methyl-3-oxo-1H-inden-4-yl)amino]benzene-acetamide; m.p. 249.5° C. (comp. 1).

Example 10

Sodium hydroxide (2.5 ml) was added to a suspension of intermediate (19) (0.006 mol) in ethanol (60 ml). Hydrogen peroxide 30% (6ml) was added dropwise at 0°–5° C. and the reaction mixture was stirred for 3 hours at 60° C. The solvent was evaporated. The residue was partitioned between $CH_2Cl_2$ and $H_2O$. The layers were separated. The aqueous layer was extracted twice with $CHCl_3$. The organic layer was separated, dried ($MgSO_4$), filtered and the solvent was evaporated. The residue was purified by column chromatography over silica gel (eluent: $CH_2Cl_2/CH_3OH$ 98/2). The pure fractions were collected and the solvent was evaporated. The residue was crystallized from $CH_3CN$. The crystals were filtered off and recrystallized from $CH_3OH$. The crystals were filtered off and dried (vacuum; 80° C.), yielding 0.32 g (15%) of (±)-2,6-dichloro-α-[( 2,3-di-hydro-3-oxo-4-benzofuranyl)amino]benzeneacetamide; mp. 245.4° C. (comp. 9)

Example 11

A mixture of 5.5 g of 1,3-dichloro-2-( 1-bromoethyl)benzene and 2.9 g of 2-(methylcarbonyl)benzeneamine was stirred for 8 hours at 100° C. After cooling, the reaction mixture was purified by column chromatography (silica gel; $CH_2Cl_2$/hexane 50:50). The eluent of the desired fraction was evaporated and the residue was triturated in hexane. The product was filtered off and dried in vacuo at 60° C., yielding 1.05 g (16.2%) of (23-1-[2-[[1-(2,6-dichlorophenyl)ethyl]amino]phenyl]ethanone; mp. 122.8° C. (comp. 10).

Example 12

A mixture of 1.03 g of α-amino-2,6-dichlorobenzeneethanol and 0.7 g of 1-fluoro-2-nitrobenzene was stirred for 3 hours at 110° C. The reaction mixture was purified by column chromatography (silica gel; $CH_2Cl_2/CH_3OH$ 98:2). The eluent of the desired fraction was evaporated and the residue was crystallized from acetonitrile. The product was filtered off and dried, yielding 0.4 g (24.4%) of (±)-2,6-dichloro-β-[( 2-nitrophenyl)amino]benzeneethanol; m.p. 127.6° C. (comp. 12).

Example 13

A mixture of intermediate (29) (0.0053 mol) in methanol (100 ml) and hydrochloric acid 6N (2 ml) was stirred for 2 hours at room temperature. The solvent was partially evaporated. The resulting precipitate was filtered off and recrystallized from $CH_3CN$. The crystals were filtered off and dried, yielding 1.1g (61.1%) (±)-1-[2-[[cyclopropyl-( 2,6-dichlorophenyl)methyl]amino]phenyl]ethanone; m.p. 116.5° C. (comp. 14)

The following compounds of formula (I-a) were prepared:

| Comp. No. | Ex. No. | $R^5$ | physical data |
|---|---|---|---|
| 1 | 9 | (2,3-dihydro-6-methyl-3-oxo-1H-inden-4-yl)-NH– | mp. 249.5° C. |
| 2 | 9 | (5,6,7,8-tetrahydronaphthalen-2-yl)-NH– | mp. 151° C. |
| 3 | 9 | (quinolin-8-yl)-NH– | mp. 221.1° C. |
| 4 | 9 | (6-nitro-2,3-dihydro-1H-inden-5-yl)-NH– | mp. 265.0° C. |
| 5 | 9 | (6-acetyl-2,3-dihydro-1H-inden-5-yl)-NH– | mp. 237.4° C. |
| 6 | 9 | (7-chloro-2,3-dihydrobenzofuran-5-yl)-NH– | mp. 201.5° C. |

-continued

[Structures shown:

Structure A: 2,6-dichlorophenyl-CH(C(=O)NH2)-NH- attached to phenyl with R5, R6, R7, R8 substituents Structure B: -NH-phenyl with R5, R6, R7, R8 substituents]

| Comp. No. | Ex. No. | R5 | physical data |
|---|---|---|---|
| 7 | 9 | 8-quinolinyl-N-oxide (—NH attached) | mp. 258.0° C. |
| 8 | 9 | 2-(formamido)benzamide linkage | mp. 274.3° C. |
| 9 | 10 | 2-propionylphenyl (—NH attached) | mp. 245.4° C. |

The following compounds of formula (I-b) were prepared:

[Structure C: 2,6-dichlorophenyl-CH(R9)-NH-phenyl(R13, R14, R15)]

[Structure D: -NH-phenyl(R5, R6, R7, R8)]

| Comp. No. | Ex. No. | R9 | R5 | physical data |
|---|---|---|---|---|
| 10 | 11 | CH3 | 2-acetylphenyl (—NH, o-C(=O)CH3) | mp. 122.8° C. |

-continued

[Structures repeated: Structure C and Structure D]

| Comp. No. | Ex. No. | R9 | R5 | physical data |
|---|---|---|---|---|
| 11 | 11 | CH2CH3 | 2-acetylphenyl | mp. 100.7° C. |
| 12 | 12 | CH2OH | 2-nitrophenyl | mp. 127.6° C. |
| 13 | 12 | CH3 | 2-nitrophenyl | mp. 141.8° C. |
| 14 | 13 | cycloC3H5 | 2-acetylphenyl | mp. 116.5° C. |

C. Pharmacological Example

Example 14

A rapid, sensitive and automated assay procedure was used for the in-vitro evaluation of anti-HIV agents. An HIV-1 transformed T4-cell line, MT-4, which was previously shown (Koyanagi et al., *Int. J. Cancer*, 36, 445–451, 1985) to be highly susceptible to and permissive for HIV infection, served as the target cell line. Inhibition of the HIV-induced cytopathic effect was used as the end point. The viability of both HIV- and mock-infected cells was assessed spectrophotometrically via the in-situ reduction of 3-(4,5-dimethylthiazol-2-yl)-2,5-diphenyltetrazolium bromide (MTT). The 50% cytotoxic dose ($CD_{50}$ in μg/ml) was defined as the concentration of compound that reduced the absorbance of the mock-infected control sample by 50%. The percent protection achieved by the compound in HIV-infected cells was calculated by the following formula:

$$\frac{(OD_T)_{HIV} - (OD_C)_{HIV}}{(OD_C)_{MOCK} - (OD_C)_{HIV}} \quad \text{expressed in \%,}$$

whereby $(OD_T)_{HIV}$ is the optical density measured with a given concentration of the test compound in HIV-infected cells; $(OD_C)_{HIV}$ is the optical density measured for the control untreated HIV-infected cells; $(OD_C)_{MOCK}$ is the optical density measured for the control untreated mock-infected cells; all optical density values were determined at 540 nm. The dose achieving 50% protection according to the above formula was defined as the 50% effective dose ($ED_{50}$ in µg/ml). The ratio of $CD_{50}$ to $ED_{50}$ was defined as the selectivity index (SI). Particular values are listed in Table 1 hereinbelow.

TABLE 1

| Co. No. | $CD_{50}$ (µg/ml) | $ED_{50}$ (µg/ml) | SI |
|---|---|---|---|
| 1 | 207 | 0.0038 | 54560 |
| 5 | 10 | 0.2 | 50 |
| 6 | 0.87 | 0.079 | 11 |
| 7 | 53 | 0.047 | 3255 |
| 9 | 168.7 | 0.12 | 1405 |
| 10 | 5 | 0.022 | 227 |
| 11 | 6.9 | 0.52 | 13 |
| 12 | 4.3 | 0.18 | 25 |
| 13 | 0.13 | 0.021 | 6 |
| 14 | 4.1 | 0.15 | 27 |

D. Composition examples

"Active ingredient (A.I.) as used throughout these examples relates to a compound of formula (I), a pharmaceutically acceptable acid addition salt or a stereochemically isomeric form thereof."

Example 15 : ORAL DROPS

500 Grams of the A.I. was dissolved in 0.5 l of 2-hydroxypropanoic acid and 1.5 l of the polyethylene glycol at 60°–80° C. After cooling to 30°–40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l , providing an oral drop solution comprising 10 mg/ml of A.I.. The resulting solution was filled into suitable containers.

Example 16 : ORAL SOLUTION

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

Example 17:CAPSULES

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelatin capsules, comprising each 20 mg of the active ingredient.

Example 18: FILM-COATED TABLETS

Preparation of tablet core

A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 ml of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 mg of the active ingredient.

Coating

To a solution of 10 grams methyl cellulose in 75 ml of denaturated ethanol there was added a solution of 5 grams of ethyl cellulose in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a coating apparatus.

Example 19: INJECTABLE SOLUTION 1.8 Grams methyl 4-hydroxybenzoate and 0.2 grams propyl 4-hydroxybenzoate were dissolved in about 0.5 l of boiling water for injection. After cooling to about 50° C. there were added while stiffing 4 grams lactic acid, 0.05 grams propylene glycol and 4 grams of the A.I.. The solution was cooled to room temperature and supplemented with water for injection q.s. ad 1 l, giving a solution comprising 4 mg/ml of A.I.. The solution was sterilized by filtration (U.S.P. XVII p. 811 ) and filled in sterile containers.

Example 20: SUPPOSITORIES

3 Grams A.I. was dissolved in a solution of 3 grams 2,3-dihydroxybutanedioic acid in 25 ml polyethylene glycol 400. 12 Grams surfactant (SPAN®) and triglycerides (Witepsol 555 ®) q.s. ad 300 grams were molten together. The latter mixture was mixed well with the former solution. The thus obtained mixture was poured into moulds at a temperature of 37°–38° C. to form 100 suppositories each containing 30 mg/ml of the A.I.

Example 21: INJECTABLE SOLUTION

60 Grams of A.I. and 12 grams of benzylalcohol were mixed well and sesame oil was added q.s. ad 1 l, giving a solution comprising 60 mg/ml of A.I. The solution was sterilized and filled in sterile containers.

Example 22:2% CREAM 75 mg Stearyl alcohol, 20 mg cetyl alcohol, 20 mg sorbitan monostearate and 10 mg isopropyl myristate are introduced into a doublewall jacketed vessel and heated until the mixture has completely molten. This mixture is added to a separately prepared mixture of purified water, 200 mg propylene glycol and 15 mg polysorbate 60 having a temperature of 70° to 75° C. while using a homogenizer for liquids. The resulting emulsion is allowed to cool to below 25° C. while continuously mixing. A solution of 20 mg of A.I. of formula (I), 1 mg polysorbate 80 and 637 mg purified water and a solution of 2 mg sodium sulfite anhydrous in purified water are next added to the emulsion while continuously mixing. The cream is homogenized and filled into suitable tubes.

Example 23 :AEROSOLS a) To a solution of 2.5 mg A.I. in 0.7 ml of distilled water there are added 730 mg of a 0.1N hydrochloric acid solution. After stirring for 10 minutes at room temperature, the pH of the thus obtained solution is adjusted to pH 5.5 by adding a 0.1N sodium hydroxide solution. Then there are added successively 4 mg of sodium chloride and 0.15 mg of phenylmercuric acetate and the whole is stirred to produce a complete solution. Distilled water is then added to a volume of 1.0 ml. The solution is filled in a glass bottle closed with a mechanical pump delivering 0.1 ml per puff upon administration.

b) To a solution of 2 mg A.I. in 0.7 ml of distilled water there are added 600 mg of a 0.1N hydrochloric acid solution. After stirring for 10 minutes at room temperature, 10 mg of polyvinylalcohol is dissolved in the mixture and the pH of the thus obtained solution is adjusted to pH 5.5 by adding a 0.1N sodium hydroxide solution. Then there are added successively 4 m g of sodium chloride and 2 mg of phenylethyl alcohol and the whole is stirred to produce a complete solution. Distilled water is added to produce a volume of 1.0 ml which is filled in a glass bottle closed with a mechanical pump spray delivering 0.1 ml per puff upon administration.

We claim:

1. A method for treating individuals infected with HIV-1 which comprises administering to said individuals a pharmaceutically effective amount of a compound of the formula:

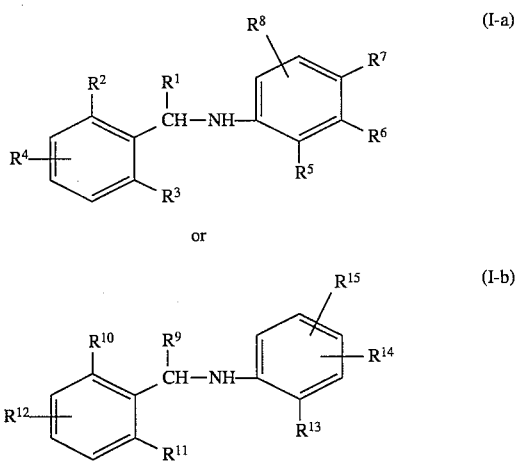

a pharmaceutically acceptable acid addition salt or a stereochemically isomeric form thereof, wherein:

$R^1$ is
trifluoromethyl, methyl carbonyl or $C_{3-6}$cycloalkyl; or
a radical —C(=X)—$NR^{16}R^{17}$, wherein X is O or S, and $R^{16}$ and $R^{17}$ each independently are hydrogen or $C_{1-4}$alkyl; or
a radical —Alk—$R^{18}$, wherein Alk is $C_{1-4}$alkanediyl, and $R^{18}$ is hydrogen or hydroxy;

$R^2$ and $R^3$ each independently are halo or methyl;

$R^4$ is hydrogen, hydroxy, halo, nitro or trifluoromethyl;

$R^8$ represents hydrogen, $C_{1-6}$alkyloxy, $C_{1-6}$alkyl, halo, nitro, aminocarbonyl, or a radical $C_{1-6}$alkyl(C=Z)—, wherein Z represents =O, =N—OH, =N—$OCH_3$, =N—$NH_2$ or =N—$N(CH_3)_2$;

$R^7$ represents hydrogen, in which case $R^5$ and $R^6$ taken together form a bivalent radical of formula —$(CH_2)_m$— wherein m is 3 or 4, —(C=O)—O—$CH_2$—, —(C=O)—O—$(CH_2)_2$—, —(C=O)—$(CH_2)_2$—, —(C=O)—$(CH_2)_3$—, —(C=O)$CH_2O$—, —(C=O)$CH_2NH$—, —(C=O)—$(CH_2)_2$—O—, —O—$(CH_2)_2$—, —O—$(CH_2)_3$—, —N=CH—CH=CH—, —(N→O)=CH—CH=CH— or —(C=O)NH—CH=N—, wherein one or two hydrogen atoms can optionally be replaced with $C_1$alkyl; or $R^6$ and $R^7$ taken together form a bivalent radical of formula —$(CH_2)_m$— wherein m is 3 or 4 and wherein one or two hydrogen atoms can optionally be replaced with $C_{1-4}$alkyl, in which case $R^5$ represents hydrogen, $C_{1-6}$alkyloxy, $C_{1-6}$alkyl, halo, nitro, aminocarbonyl, or a radical $C_{1-6}$alkyl—(C=Z)—, wherein Z is as defined above;

$R^9$ is
trifluoromethyl, methylcarbonyl or $C_{3-6}$cycloalkyl; or
a radical —Alk—$R^{19}$, wherein Alk is $C_{1-4}$alkanediyl and $R^{19}$ is hydrogen or hydroxy;

$R^{10}$ and $R^{11}$ each independently are halo or methyl;

$R^{12}$ is hydrogen, hydroxy, halo, nitro or trifluoromethyl;

$R^{13}$ represents $C_{1-6}$alkyloxy, nitro, trifluoromethoxy, 2,2,2-trifluoroethoxy, (trifluoromethyl)carbonyl, aminocarbonyl, (cyclopropyl)carbonyl or a radical $C_{1-6}$alkyl-(C=Z)— wherein Z is as defined hereinabove; and $R^{14}$ and $R^{15}$ each independently are hydrogen, halo, $C_{1-4}$alkyl, nitro, $C_{1-4}$alkyloxy or trifluoromethyl.

2. The method of claim 1 wherein the compound is defined by Formula (I-a), and wherein $R^1$ is a radical —C(=X)$NR^{16}R^{17}$, wherein X is O or S, $R^{16}$ and $R^{17}$ each independently are hydrogen or $C_{1-4}$alkyl $R^2$ and $R^3$ are halo; and $R^4$ is hydrogen or halo.

3. The method of claim 2 wherein the compound is:
α-[(6-acetyl-2,3-dihydro-1H-inden-5-yl)amino]-2,6-dichloro-benzeneacetamide;

2,6-dichloro-α-[(5-chloro-2,3-dihydro-7-benzofuranyl)amino]-benzeneacetamide;

2,6-dichloro-α-α(2,3-dihydro-6-methyl-3-oxo-1H-inden-4-yl)amino]-benzeneacetamide;

2,6-dichloro-α-[(8-quinolinylamino)benzeneacetamide-1-oxide;

2,6-dichloro-α-[(2,3-dihydro-3-oxo-4-benzofuranyl)amino]-benzeneacetamide; or a pharmaceutically acceptable acid addition salt or a stereochemically isomeric form thereof.

4. A method according to claim 1 wherein the compound is defined by Formula (I-b) and wherein $R^9$ is cyclopropyl or a radical —Alk—$R^{19}$; wherein $R^{10}$ and $R^{11}$ are halo; and wherein $R^{12}$ is hydrogen or halo.

5. A method according to claim 4 wherein the compound is:

2,6 -dichloro-α-methyl-N- ( 2 -nitrophenyl)benzenemethaneamine;

1-[2-[[1- (2,6-dichlorophenyl)ethyl]amino]phenyl]ethanone;

2,6-dichloro-α-[(2-nitrophenyl)amino]benzeneethanol;

1-[2-[[1-(2,6-dichlorophenyl)propyl]amino]phenyl]ethanone;

1-[2-[[cyclopropyl(2,6-dichlorophenyl)methyl]amino]phenyl]ethanone; or a pharmaceutically acceptable acid addition salt or a stereochemically isomeric form thereof.

* * * * *